United States Patent
Lloyd (10) Patent No.: US 9,664,660 B2
(45) Date of Patent: May 30, 2017

(54) AIR SENSOR WITH AIR FLOW CONTROL

(71) Applicant: InvenSense, Inc., San Jose, CA (US)

(72) Inventor: Stephen Lloyd, Los Altos, CA (US)

(73) Assignee: INVENSENSE, INC., San Jose, CA (US)

( * ) Notice: Subject to any disclaimer, the term of this patent is extended or adjusted under 35 U.S.C. 154(b) by 163 days.

(21) Appl. No.: 14/595,903

(22) Filed: Jan. 13, 2015

(65) Prior Publication Data

US 2016/0202224 A1   Jul. 14, 2016

(51) Int. Cl.
*G01N 33/00* (2006.01)
*G01K 13/02* (2006.01)
*F16K 31/02* (2006.01)
*G05D 7/01* (2006.01)
*H04R 1/28* (2006.01)
*H04R 19/00* (2006.01)

(52) U.S. Cl.
CPC ......... *G01N 33/0016* (2013.01); *F16K 31/02* (2013.01); *G01K 13/02* (2013.01); *G05D 7/01* (2013.01); *G01K 2013/024* (2013.01); *H04R 1/2811* (2013.01); *H04R 19/005* (2013.01); *H04R 2201/003* (2013.01); *H04R 2499/11* (2013.01)

(58) Field of Classification Search
CPC ..... F16K 31/02; H04R 19/005; H04R 1/2811; H04R 2201/003; H04R 2499/11
See application file for complete search history.

(56) References Cited

U.S. PATENT DOCUMENTS

| | | | |
|---|---|---|---|
| 8,692,340 B1* | 4/2014 | Ata | B81B 3/001 257/415 |
| 2003/0231967 A1 | 12/2003 | Najafi et al. | |
| 2013/0241045 A1* | 9/2013 | Goida | B81B 7/0061 257/704 |
| 2014/0361388 A1* | 12/2014 | Chan | B81B 3/0021 257/416 |
| 2015/0158722 A1* | 6/2015 | Lim | B81B 7/02 257/416 |

* cited by examiner

*Primary Examiner* — Francis Gray
(74) *Attorney, Agent, or Firm* — McAndrews, Held & Malloy, Ltd.

(57) ABSTRACT

A system and method for providing and/or controlling air flow to an air sensor. As a non-limiting example, an air sensor system may include mechanical and/or electromechanical features (e.g., MEMS features) to control air flow to an air sensor. Various aspects of the disclosure may, for example, be implemented in a personal electronic device.

19 Claims, 7 Drawing Sheets

AIR SENSOR WITH AIR FLOW CONTROL

CROSS-REFERENCE TO RELATED APPLICATIONS/INCORPORATION BY REFERENCE

This application is related to U.S. patent application Ser. No. 14/273,845, titled "INTEGRATED PACKAGE CONTAINING MEMS ACOUSTIC SENSOR AND ENVIRONMENTAL SENSOR AND METHODOLOGY FOR FABRICATING SAME," and filed on May 9, 2014, the entire contents of which are hereby incorporated herein by reference in their entirety.

FEDERALLY SPONSORED RESEARCH OR DEVELOPMENT

[Not Applicable]

SEQUENCE LISTING

[Not Applicable]

MICROFICHE/COPYRIGHT REFERENCE

[Not Applicable]

BACKGROUND

Various electronic devices, for example consumer electronic devices, include air sensors. Such air sensors are often, however, isolated. Further limitations and disadvantages of conventional and traditional approaches will become apparent to one of skill in the art, through comparison of such approaches with the disclosure as set forth in the remainder of this application with reference to the drawings.

SUMMARY

Various aspects of this disclosure provide an air sensor with air flow control. As a non-limiting example, an air sensor system may comprise mechanical and/or electromechanical features (e.g., MEMS features) to control air flow to an air sensor. Advantages, aspects and novel features of the present invention, as well as details of an illustrated embodiment thereof, will be more fully understood from the following description and drawings.

DETAILED DESCRIPTION OF VARIOUS ASPECTS OF THE DISCLOSURE

The following discussion presents various aspects of the present disclosure by providing various examples thereof. Such examples are non-limiting, and thus the scope of various aspects of the present disclosure should not necessarily be limited by any particular characteristics of the provided examples. In the following discussion, the phrases "for example," "e.g.," and "exemplary" are non-limiting and are generally synonymous with "by way of example and not limitation," "for example and not limitation," and the like.

The following discussion may at times utilize the phrase "A and/or B." Such phrase should be understood to mean just A, or just B, or both A and B. Similarly, the phrase "A, B, and/or C" should be understood to mean just A, just B, just C, A and B, A and C, B and C, or all of A and B and C.

The following discussion may at times utilize the phrases "operable to," "operates to," and the like in discussing functionality performed by particular hardware, including hardware operating in accordance with software or other code instructions. The phrases "operates to," "is operable to," and the like include "operates when enabled to." For example, a module that operates to perform a particular operation, but only after receiving a signal to enable such operation, is included by the phrases "operates to," "is operable to," and the like. Moreover, a module is "operable to" or "operates to" perform a function whenever the module comprises the necessary hardware and software or other code (if any is necessary) to perform the function, regardless of whether performance of the function is disabled or not enabled (e.g., by a user-configurable setting, factory trim, etc.).

The following discussion may at times refer to various system or device functional modules. It should be understood that the functional modules were selected for illustrative clarity and not necessarily for providing distinctly separate hardware and/or software modules. For example, any one or more of the modules discussed herein may be implemented by shared hardware, including for example a shared processor. Also for example, any one or more of the modules discussed herein may share software portions, including for example subroutines. Additionally for example, any one or more of the modules discussed herein may be implemented with independent dedicated hardware and/or software. Accordingly, the scope of various aspects of this disclosure should not be limited by arbitrary boundaries between modules unless explicitly claimed. Additionally, it should be understood that when the discussion herein refers to a module performing a function, the discussion is generally referring to either a pure hardware module implementation and/or a processor operating in accordance with software. Such software may, for example, be stored on a non-transitory machine-readable medium.

In various example embodiments discussed herein, a chip is defined to include at least one substrate typically formed from a semiconductor material. A single chip may for example be formed from multiple substrates, where the substrates are mechanically bonded and electrically connected to preserve the functionality. Multiple chip (or multi-chip) includes at least two substrates, wherein the two substrates are electrically connected, but do not require mechanical bonding.

A package provides electrical connection between the bond pads on the chip (or for example a multi-chip module) and a metal lead that can be soldered to a printed circuit board (or PCB). A package typically comprises a substrate and a cover. An Integrated Circuit (IC) substrate may refer to a silicon substrate with electrical circuits, typically CMOS circuits. A MEMS substrate provides mechanical support for the MEMS structure(s). The MEMS structural layer is attached to the MEMS substrate. The MEMS substrate is also referred to as handle substrate or handle wafer. In some embodiments, the handle substrate serves as a cap to the MEMS structure.

In the described embodiments, an electronic device incorporating a sensor may, for example, employ a sensor processing module also referred to as Sensor Processing Unit (SPU) that includes at least one sensor in addition to electronic circuits. In various example implementations the SPU may, for example, be autonomous or may be integrated with a Motion Processing Unit (MPU). As discussed herein, the SPU or any portion thereof may be implemented by a host or application processor. The at least one sensor may comprise any one or more of a variety of sensors, such as for example a gyroscope, a compass, a magnetometer, an accelerometer, a microphone, a pressure sensor, a proximity sensor, a moisture sensor, a temperature sensor, a chemical biometric sensor, or an ambient light sensor, among others known in the art.

Some embodiments may, for example, comprise an accelerometer, gyroscope, and magnetometer or other compass technology, which each provide a measurement along three axes that are orthogonal relative to each other, and may be referred to as 9-axis devices. Other embodiments may, for example, comprise an accelerometer, gyroscope, compass, and pressure sensor, and may be referred to as 10-axis devices. Other embodiments may not include all the sensors or may provide measurements along one or more axes.

The sensors may, for example, be formed on a first substrate. Various embodiments may, for example, include solid-state sensors and/or any other type of sensors. The electronic circuits in the SPU may, for example, receive measurement outputs from the one or more sensors. In various embodiments, the electronic circuits process the sensor data. The electronic circuits may, for example, be implemented on a second silicon substrate. In some embodiments, the first substrate may be vertically stacked, attached and electrically connected to the second substrate in a single semiconductor chip, while in other embodiments, the first substrate may be disposed laterally and electrically connected to the second substrate in a single semiconductor package (e.g., both attached to a common packaging substrate or other material). In other embodiments, the sensors may, for example, be formed on different respective substrates (e.g., all attached to a common packaging substrate or other material).

In an example embodiment, the first substrate is attached to the second substrate through wafer bonding, as described in commonly owned U.S. Pat. No. 7,104,129, which is hereby incorporated herein by reference in its entirety, to simultaneously provide electrical connections and hermetically seal the MEMS devices. This fabrication technique advantageously enables technology that allows for the design and manufacture of high performance, multi-axis, inertial sensors in a very small and economical package. Integration at the wafer-level minimizes parasitic capacitances, allowing for improved signal-to-noise relative to a discrete solution. Such integration at the wafer-level also enables the incorporation of a rich feature set which minimizes the need for external amplification.

In the described embodiments, raw data refers to measurement outputs from the sensors which are not yet processed. Motion data refers to processed raw data. Processing may, for example, comprise applying a sensor fusion algorithm or applying any other algorithm. In the case of a sensor fusion algorithm, data from one or more sensors may be combined and/or processed to provide an orientation of the device. In the described embodiments, an SPU may include processors, memory, control logic and sensors among structures.

The discussion herein may generally refer to signals, for example signals comprising sensor values, compensated values, coefficients, etc. It should be understood that a "signal" in such context may, for example, comprise a discrete time signal corresponding to a sequence of values over time. For example, a gyroscope measurement signal may, for example, comprise a sequence of gyroscope output values that update at an update rate. For illustrative simplicity, the following discussion will address analyzing various sensor signal values over time, for example discrete time signals, to determine device or user attitude or orientation. The scope of this disclosure is not, however, limited to a particular format of such signals unless explicitly stated. For example, such a signal may also comprise a sequence of digital amplitudes and/or an analog signal.

Among the various challenges of environmental sensors is that, for an accurate measurement of the environment, a representative sample of the environment is desirable. For various reasons (e.g., manufacturing reasons, circuit protection reasons, etc.), a sensor may be isolated from the environment to be sensed. For example, a sensor might be embedded in an isolated location and/or compartment of a phone, watch, eyeglass, ring, any of a variety of types consumer electronics device, etc. Additionally, the device incorporating the sensor and/or other nearby devices may locally affect the environment being measured. For example, a consumer electronic device may generate substantial amounts of heat due to its electronics, due to proximity to a user's body, due to solar heating, etc. Even in system architectures in which a sensor is effectively isolated from other components of the system that may adversely affect the sensor's readings, the sensor may still be isolated from the environment to be measured.

In various sensor system implementations, for example those including sensors that measure aspects of air, exposing the sensor to the air of interest is beneficial. Various aspects of this disclosure provide a variety of sensor system aspects, including passive and/or active mechanical system components, control processing, etc., that enhance the sensor's exposure to the air of interest. Such sensor system aspects, for example, may comprise air-moving features, air channel features, air flow control features, etc. Example sensors may, for example, include sensors that measure temperature, humidity, gas, pressure, chemical, biological parameters, particles, nanoparticles, spores, pathogens, breath, pollution, carbon monoxide, etc. Accordingly, various aspects of this disclosure provide an air sensor with air flow control. As a non-limiting example, an air sensor system may include mechanical and/or electromechanical features (e.g., MEMS features) to control air flow to an air sensor.

Figure 1:
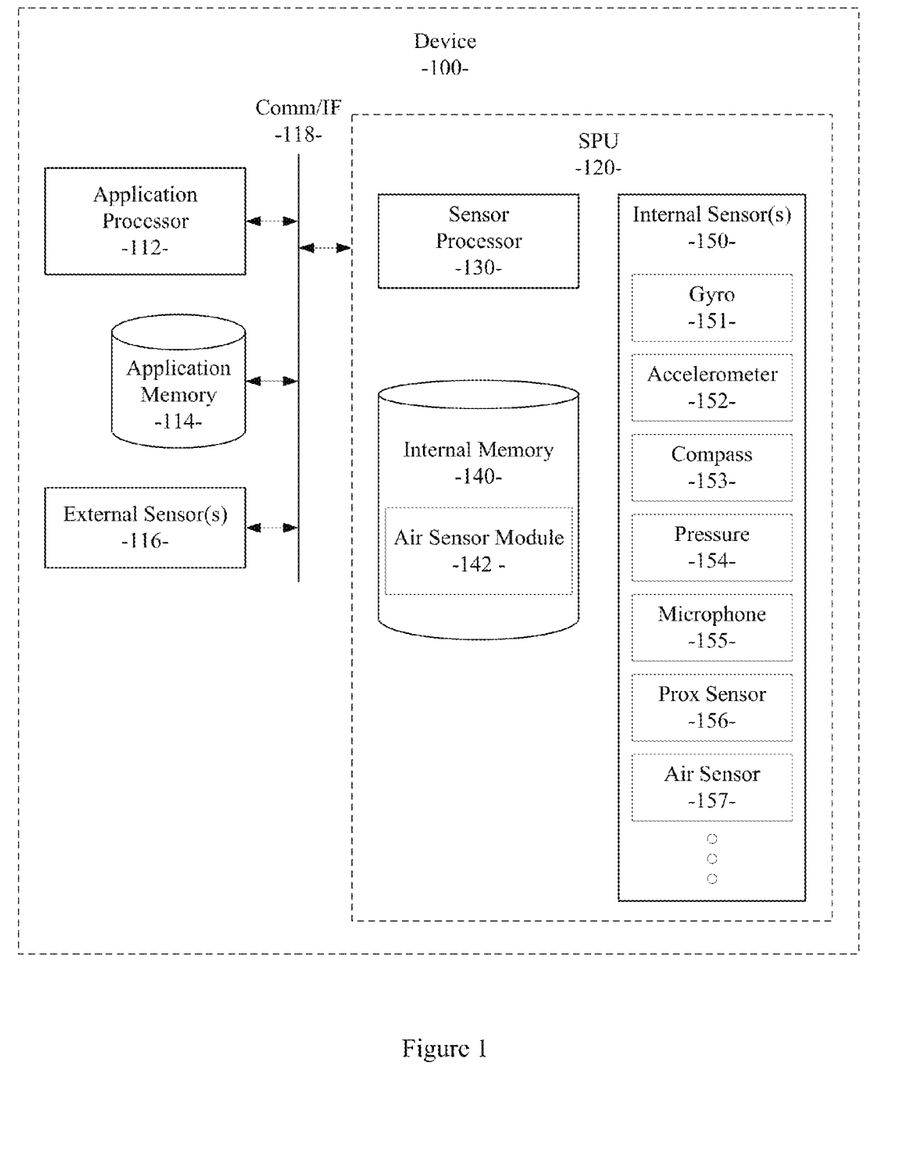
FIG. 1 shows a block diagram of an example electronic device comprising an air sensor, in accordance with various aspects of the present disclosure.

Turning first to FIG. 1, such figure shows a block diagram of an example electronic device 100 comprising an air sensor and/or sensor air flow control, in accordance with various aspects of the present disclosure. As will be appreciated, the device 100 may be implemented as a device or apparatus, such as a handheld and/or wearable device that can be moved in space by a user, and its motion and/or orientation in space therefore sensed, characteristics of the environment in which it is operating may be sensed, etc. For example, such a handheld and/or wearable device may comprise a mobile phone (e.g., a cellular phone, a phone running on a local network, or any other telephone handset), wired telephone (e.g., a phone attached by a wire and/or optical tether), personal digital assistant (PDA), pedometer, personal activity and/or health monitoring device, video game player, video game controller, navigation device, mobile internet device (MID), personal navigation device (PND), digital still camera, digital video camera, binoculars, telephoto lens system, portable music, video, or media player, remote control, or other handheld device, headset, eyeglasses, watch, ring, or a combination of one or more of these devices.

In some embodiments, the device 100 may be a self-contained device that comprises its own display and/or other user output devices in addition to various user input devices. However, in other embodiments, the device 100 may function in conjunction with another portable device or a non-portable device such as a desktop computer, electronic tabletop device, server computer, smart phone, etc., which can communicate with the device 100, e.g., via network connections. The device 100 may, for example, be capable of communicating via a wired connection using any type of wire-based communication protocol (e.g., serial transmissions, parallel transmissions, packet-based data communications), wireless connection (e.g., electromagnetic radiation, infrared radiation or other wireless technology), or a combination of one or more wired connections and one or more wireless connections.

As shown, the example device 100 comprises an SPU 120, application (or host) processor 112, application (or host) memory 114, and may comprise one or more sensors, such as external sensor(s) 116. The application processor 112 may, for example, be configured to perform the various computations and operations involved with the general function of the device 100 (e.g., running applications, performing operating system functions, performing power management functionality, controlling user interface functionality for the device 100, etc.). The application processor 112 may, for example, be coupled to SPU 120 through a communication interface 118, which may be any suitable bus or interface, such as a peripheral component interconnect express (PCIe) bus, a universal serial bus (USB), a universal asynchronous receiver/transmitter (UART) serial bus, a suitable advanced microcontroller bus architecture (AMBA) interface, an Inter-Integrated Circuit (I2C) bus, a serial digital input output (SDIO) bus, or other equivalent. The application memory 114 may, for example, comprise programs, drivers or other data that utilize information provided by the SPU 120. Details regarding example suitable configurations of the application (or host) processor 112 and SPU 120 may be found in co-pending, commonly owned U.S. patent application Ser. No. 12/106,921, filed Apr. 21, 2008, which is hereby incorporated herein by reference in its entirety.

In this example embodiment, the SPU 120 is shown to comprise a sensor processor 130, internal memory 140 and one or more internal sensors 150. The internal sensors 150 comprise a gyroscope 151, an accelerometer 152, a compass 153 (for example a magnetometer), a pressure sensor 154, a microphone 155, a proximity sensor 156, and an air sensor 157. Though not explicitly shown, the internal sensors 150 may comprise any of a variety of sensors. All or some of the internal sensors 150 may, for example, be implemented as MEMS-based motion sensors, including inertial sensors such as a gyroscope or accelerometer, electromagnetic sensors such as a Hall effect or Lorentz field magnetometer, various air sensors, etc. As desired, one or more of the internal sensors 150 may be configured to provide raw data output measured along three orthogonal axes or any equivalent structure. The internal memory 140 may store algorithms, routines or other instructions for processing data output by one or more of the internal sensors 150 and/or for controlling operation of one or more of the internal sensors 150, including the air sensor module 142. If provided, external sensor(s) 116 may comprise one or more sensors, such as accelerometers, gyroscopes, magnetometers, pressure sensors, microphones, proximity sensors, and ambient light sensors, air sensors, biometric sensors, temperature sensors, and moisture sensors, among other sensors. As used herein, an internal sensor generally refers to a sensor implemented, for example using MEMS techniques, for integration with the SPU 120 into a single chip. Similarly, an external sensor as used herein generally refers to a sensor carried on-board the device 100 that is not integrated into the SPU 120. For example, an external sensor may located in a same package as the SPU (e.g., in a multi-chip single-package module). Also for example, an external sensor may be located in a same electronic device as the SPU but in a different package. Further for example, an external sensor may be located outside the electronic device that houses the SPU.

Even though various embodiments may be described herein in the context of internal sensors implemented in the SPU 120, these techniques may be applied to a non-integrated sensor, such as an external sensor 116, and likewise the air sensor module 142 may be implemented using instructions stored in any available memory resource, such as for example the application memory 114, and may be executed using any available processor, such as for example the application processor 112. Also for example, any portion of or all of the entire air sensor module 142 may be implemented in a distributed system, for example coupled to the device 100 via a communication network. Still further, the functionality performed by the air sensor module 142 may be implemented using any combination of hardware, firmware and software.

As will be appreciated, the application (or host) processor 112 and/or sensor processor 130 may be one or more microprocessors, central processing units (CPUs), microcontrollers or other processors, which run software programs for the device 100 and/or for other applications related to the functionality of the device 100. For example, different software application programs such as menu navigation software, games, camera function control, navigation software, environmental monitoring programs, health monitoring programs, and telephone, or a wide variety of other software and functional interfaces, can be provided. In some embodiments, multiple different applications can be provided on a single device 100, and in some of those embodiments, multiple applications can run simultaneously on the device 100. Multiple layers of software can, for example, be provided on a computer readable medium such as electronic memory or other storage medium such as hard disk, optical disk, flash drive, etc., for use with application processor 112 and sensor processor 130. For example, an operating system layer can be provided for the device 100 to control and manage system resources in real time, enable functions of application software and other layers, and interface application programs with other software and functions of the device 100. In various example embodiments, one or more motion algorithm layers may provide motion algorithms for lower-level processing of raw sensor data provided from internal or external sensors. Further, a sensor device driver layer may provide a software interface to the hardware sensors of the device 100. Some or all of these layers can be provided in the application memory 114 for access by the application processor 112, in internal memory 140 for access by the sensor processor 130, or in any other suitable architecture (e.g., including distributed architectures).

In some example embodiments, it will be recognized that the example architecture depicted in FIG. 1 may provide for air sensor processing and/or air flow control to be performed using the SPU 120 and might not require involvement of the application (or host) processor 112 and/or application memory 114. Such example embodiments may, for example, be implemented with one or more internal sensors 150 on a single chip and/or a multi-chip. Moreover, as will be described below, air sensor processing and/or air flow control may be implemented using computationally efficient algorithms to reduce processing overhead and power consumption.

As mentioned herein, an air sensor module may be implemented by a processor (e.g., the sensor processor 130) operating in accordance with software instructions (e.g., the air sensor module 142 stored in the internal memory 140), or by a pure hardware solution. The discussion of various figures herein will provide further example details of at least the operation of the air sensor module 142 (e.g., when executed by a processor such as the sensor processor 130). It should be understood that any or all of the functional modules discussed herein may be implemented in a pure hardware implementation and/or by a processor operating in accordance with software instructions. It should also be understood that any or all software instructions may be stored in a non-transitory computer-readable medium.

The discussion will now turn to various aspects of the air sensor 157 and/or air sensor module 142. As explained above, it should be noted that the air sensor 157 may be included as part of the SPU 120, included as part of the device 100 separate from the SPU 120, and/or may be external to the device 100 (e.g., in a different user device, in a wearable device, in an automobile, in a home, in an office, etc.) and communicatively coupled to the device 100, etc. The air sensor 157 (whether internal to the SPU 120 and/or device 100, or external) may share any or all characteristics with any of the sensor systems illustrated and discussed herein.

Various aspects of this disclosure utilize a speaker for causing air to move over a sensor. Though a speaker is often presented as an example, it should be noted that the scope of various aspects of this disclosure is not limited by the utilization of and/or characteristics of speakers. For example, a speaker, a vibrator, cooling fan, or any other device (e.g., the primary purpose of which is not to move air through or over a sensor) may be utilized. Also for example, a fan or any other device (e.g., the primary purpose of which is to move air through or over a sensor) may be utilized.

Figure 2A:
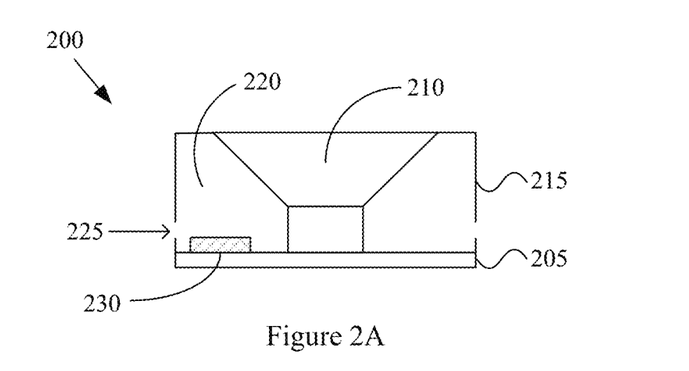
FIGS. 2A-2C show block diagrams of example speaker assemblies with integrated air sensors, in accordance with various aspects of the present disclosure.

FIG. 2A shows a block diagram (e.g., a cross-sectional view) of an example speaker assembly 200 with an integrated air sensor, in accordance with various aspects of the present disclosure. The example speaker assembly 200 may, for example, comprise a substrate 205. The substrate 205 may, for example, comprise an electronics substrate (e.g., a printed circuit board, packaging substrate, motherboard substrate, etc.), strictly mechanical substrate (e.g., glass substrate, metal substrate, insulator substrate, etc.), MEMS substrate, etc. The speaker 210 may, for example, be electrically and/or mechanically coupled to the substrate 205.

The speaker assembly 200 may also, for example, comprise walls 215. The walls 215 may, for example, comprise walls of a component cap, an EMI shield, a mechanical spacer, printed wire board, silicon, etc. The walls 215 may, for example, be coupled to the substrate 205 (e.g., soldered, epoxied with conductive and/or non-conductive adhesive, etc.). The walls 215 may also, for example, be coupled to a rim of the speaker 210, for example sealed to the outer perimeter of the radiator of the speaker 210 (e.g., at the perimeter of the speaker cone, sound forming membrane, etc.). The walls 215, the substrate may 205, and the speaker 210 may thus, for example, define a back cavity 220 for the speaker 210.

The walls 215 may, for example, comprise one or more ports 225 that allow air to flow to and/or from the back cavity 220 during operation of the speaker 210. The port 225 may, for example, be a simple hole or may alternatively comprise an opening between the back cavity 220 and an air channel defined by other components. Non-limiting examples of such air channels are presented herein.

The speaker assembly 200 may also comprise at least one air sensor 230 that is positioned in the back cavity 220. The air sensor 230 may, for example, comprise characteristics of any of a variety of air sensor types. For example, the air sensor 230 may comprise characteristics of a sensor that measures temperature, humidity, gas, pressure, chemical make-up, absence or presence of a particular gas, biological parameters, particles, nanoparticles, spores, pathogens, breath, pollution, carbon monoxide, etc. The air sensor 230 may, for example, be electrically and/or mechanically coupled to the substrate 205. The air sensor 230 may also, for example, be formed directly on the substrate 205.

In an example implementation, the air sensor 230 may be positioned adjacent to the port 225. For example, the air sensor 230 may be positioned immediately adjacent to the port. Also for example, the air sensor 230 may be positioned adjacent to the port 225 such that there are no intervening components between the air sensor 230 and the port 225. Additionally, for example, the air sensor 230 may be positioned within 1 mm of the port 225 (or alternatively within 2 mm or 5 mm).

Figure 2B:
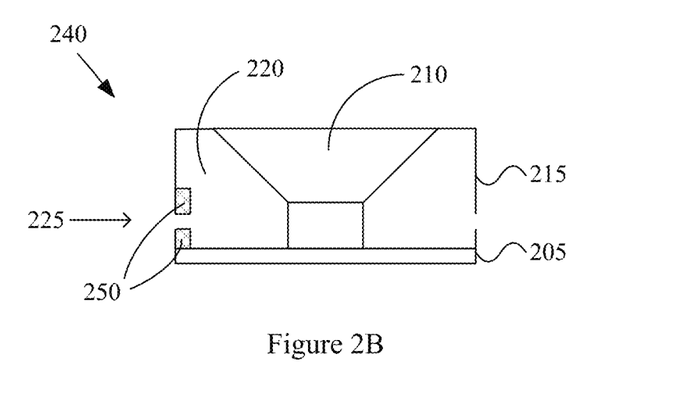

Turning next to FIG. 2B, such figure shows a block diagram (e.g., a cross-sectional view) of an example speaker assembly 240 with at least one integrated air sensor, in accordance with various aspects of the present disclosure. The example speaker assembly 240 may, for example, share any or all characteristics with the example speaker assembly 200 of FIG. 2A.

The example speaker assembly 240 may, for example, comprise an air sensor 250 that is positioned around the port 225 (e.g., partially around the port 225, completely surrounding the port 225, etc.). For example, the air sensor 250 may generally comprise a circular, square, or generally polygonal shape with a center hole through which air flowing through the port 225 also flows. The air sensor 250 may, for example, be coupled to the wall 215 and/or substrate 205. For example, the air sensor 250 may be mechanically coupled to the wall 215 and/or substrate 205 (e.g., utilizing an adhesive, solder, etc.), and electrically coupled to the substrate 205 (e.g., electrically coupled via direct-attach, via wire-bonding, etc.). Also for example, the air sensor 250 may be electrically coupled to the wall 215, which in turn is electrically coupled to the substrate 205. As shown in FIG. 2B, the air sensor 250 may be positioned in the back cavity 220 of the speaker assembly 240. In an alternative implementation, the air sensor may be positioned outside of the back cavity.

Figure 2C:
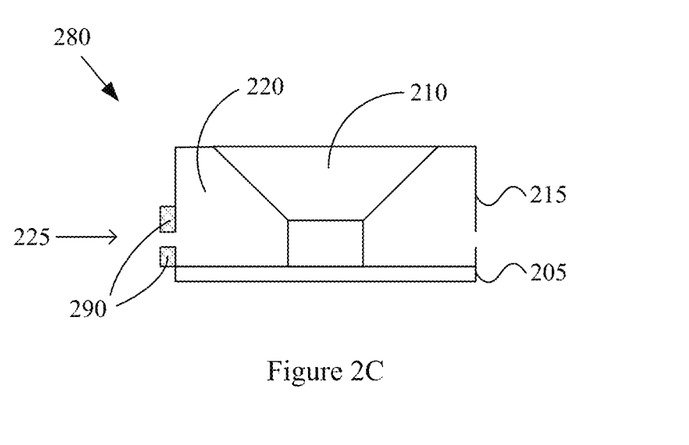

Turning next to FIG. 2C such figure shows a block diagram (e.g., a cross-sectional view) of an example speaker assembly 280 with at least one integrated air sensor, in accordance with various aspects of the present disclosure. The example speaker assembly 280 may, for example, share any or all characteristics with the example speaker assemblies 200 and 240 of FIGS. 2A and 2B, respectively.

The example speaker assembly 280 may, for example, comprise an air sensor 290 that is positioned around the port 225 (e.g., partially around the port 225, completely surrounding the port 225, etc.). For example, the air sensor 290 may generally comprise a circular, square, or generally polygonal shape with a center hole through which air flowing through the port 225 also flows. The air sensor 290 may, for example, be coupled to the wall 215 and/or substrate 205. For example, the air sensor 290 may be mechanically coupled to the wall 215 and/or substrate 205 (e.g., utilizing an adhesive, solder, etc.), and electrically coupled to the substrate 205 or another substrate (e.g., electrically coupled via direct-attach, via wire-bonding, etc.). Also for example, the air sensor 290 may be electrically coupled to the wall 215, which in turn is electrically coupled to the substrate 205. As shown in FIG. 2C, the air sensor 290 may be positioned immediately adjacent to but outside of the back cavity 220 of the speaker assembly 280.

As discussed with regard to FIGS. 2A-2C, the air sensor may be positioned within the back cavity of a speaker and/or attached to back cavity walls of the speaker immediately adjacent to the back cavity. In accordance with various aspects of the present disclosure, the air sensor may be positioned outside of a speaker component, for example coupled to a substrate (e.g., a packaging substrate, motherboard substrate, etc.) separate from the speaker component.

Figure 3A:
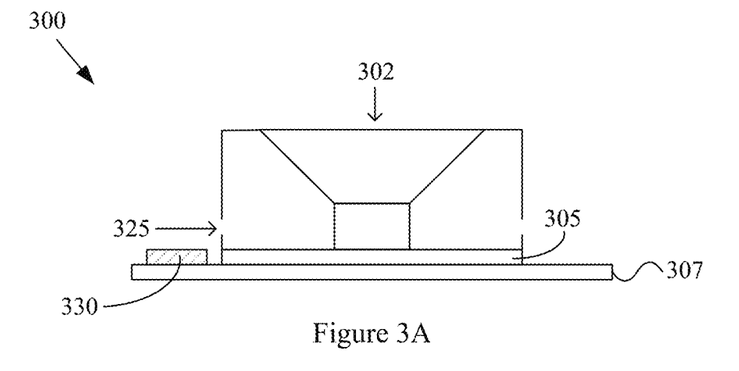
FIGS. 3A-3B show block diagrams of example speaker assemblies with substrate-mounted air sensors, in accordance with various aspects of the present disclosure.

Turning next to FIG. 3A, such figure shows a block diagram (e.g., a cross-sectional view) of an example speaker assembly 300 with at least one substrate-mounted air sensor, in accordance with various aspects of the present disclosure. The example speaker assembly 300 may, for example, comprise a substrate 307. The substrate 307 may, for example, comprise a packaging substrate, an interposer, a motherboard substrate, etc. The substrate 307 may, for example, comprise printed circuit board material, silicon, glass, metal, etc.

The example speaker assembly 300 may also, for example, comprise a speaker component 302 that is electrically and/or mechanically coupled to the substrate 307. The speaker component 302 may, for example, share any or all characteristics with the speaker assemblies 200, 240, and 280 illustrated in FIGS. 2A-2C and discussed herein. The speaker component 302 may, for example, be coupled to the substrate 307 with or without an intervening substrate 305. The speaker component 302 may, for example, be coupled to the substrate 307 utilizing conductive balls positioned between the substrate 305 and the substrate 307 and then reflowed.

The example speaker assembly 300 may also, for example, comprise an air sensor 330 mechanically and/or electrically coupled to the substrate 307. The air sensor 330 may, for example, be positioned adjacent to the speaker component 302 (e.g., directly adjacent to the speaker component 302, with no intervening components between the air sensor 330 and the speaker component 302, etc.). The air sensor 330 may, for example, be positioned adjacent to a port 325 of the speaker component 302. Also for example, the air sensor 330 may be positioned adjacent to the port 325 such that there are no intervening components between the air sensor 330 and the port 325. Additionally, for example, the air sensor 330 may be positioned within 1 mm of the port 325 (or alternatively within 2 mm or 5 mm). For example, the air sensor 330 may be positioned adjacent to the port 325 such that air flow through the port 325 must generally pass over the air sensor 330.

Figure 3B:
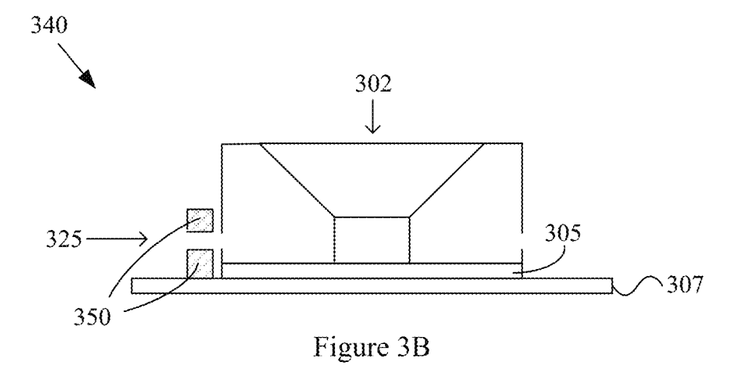

Turning next to FIG. 3B, such figure shows a block diagram (e.g., a cross-sectional view) of an example speaker assembly 340 with at least one substrate-mounted air sensor, in accordance with various aspects of the present disclosure. The example speaker assembly 340 may, for example, share any or all characteristics with the example speaker assembly 300 of FIG. 3A.

The example speaker assembly 340 may, for example, comprise an air sensor 350 that is positioned around the port 325 (e.g., partially around the port 325, completely surrounding the port 325, etc.). For example, the air sensor 350 may generally comprise a circular, square, or generally polygonal shape with a center hole through which air flowing through the port 325 also flows. The air sensor 350 may, for example, be coupled to the substrate 307 adjacent to the speaker component 302. For example, the air sensor 350 may be mechanically and/or electrically coupled to the substrate 307 (e.g., utilizing an adhesive, solder, etc.). For example, the sensor 350 may be positioned close enough to the speaker component 302 to make contact with the speaker component 302. Additionally, for example, the air sensor 350 may be positioned within 1 mm of the port 325 (or alternatively within 2 mm or 5 mm). For example, the air sensor 350 may be positioned adjacent to the port 325 such that air flow through the port 325 must generally pass over or through the air sensor 350. Though not illustrated, in an implementation in which there is a gap between the speaker component 302 and the sensor 350, there may be a seal or gasket positioned between the speaker component 302 and the sensor 350, for example to assist in guiding air flow through the sensor 350.

As discussed with regard to FIGS. 3A and 3B, the air sensor may be coupled to a substrate, for example a same substrate to which a speaker component is coupled. In accordance with various aspects of the present disclosure, the air sensor may also be coupled to a cover mounted over the speaker component.

Figure 4A:
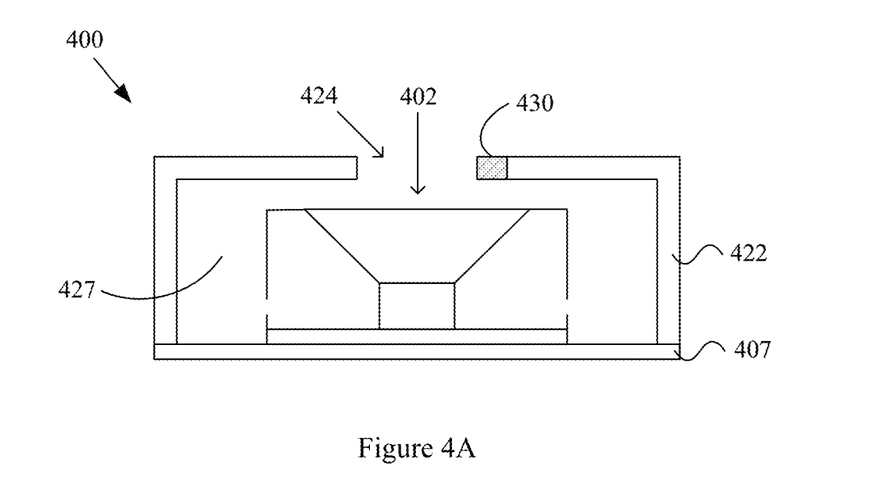
FIGS. 4A-4B show block diagrams of example speaker assemblies with cover-mounted air sensors, in accordance with various aspects of the present disclosure.

Turning next to FIG. 4A, such figure shows a block diagram (e.g., a cross-sectional view) of an example speaker assembly 400 with at least one cover-mounted air sensor, in accordance with various aspects of the present disclosure. The example speaker assembly 400 may, for example, share any or all characteristics with any other speaker assembly discussed herein (e.g., speaker assemblies 200, 240, and 280 of FIGS. 2A-2C; speaker assemblies 300 and 340 of FIGS. 3A and 3B, etc.).

The example speaker assembly 400 may, for example, comprise a substrate 407. The substrate 407 may, for example, comprise a packaging substrate, an interposer, a motherboard substrate, etc. The substrate 407 may, for example, comprise printed circuit board material, silicon, glass, metal, etc.

The example speaker assembly 400 may also, for example, comprise a speaker component 402 that is electrically and/or mechanically coupled to the substrate 407. The speaker component 402 may, for example, share any or all characteristics with the speaker assemblies 200, 240, and 280 illustrated in FIGS. 2A-2C and discussed herein. The speaker component 402 may, for example, be coupled to the substrate 407 with or without an intervening substrate. The speaker component 402 may, for example, be coupled to the substrate 407 utilizing solder, an adhesive, etc.

The example speaker assembly 400 may, for example, comprise a cover 422 that is coupled to the substrate 407. The cover 422 may, for example, comprise an electronic package cover, an overall cover or chassis of an electronic device in which the speaker component 402 is positioned, etc. The cover 422 may, for example, be formed of plastic, metal, silicon, MEMS material, glass, etc. The cover 422 may be coupled to the substrate 407 in any of a variety of manners. For example, the substrate 407 may be mechanically mounted in an overall device cover or chassis of which the cover 422 is at least a part, the cover 422 may be soldered or adhered to the substrate 407, etc.

The cover 422 may, for example, comprise a sound hole 424 formed therein. For example, the sound hole 424 may comprise a speaker port or sound hole in a chassis of an electronic device into which the speaker component 402 is mounted, an opening in an electronic circuit package cover of an electronic package in which the speaker component 402 is housed, etc. For example, the sound hole 424 may open to the environment outside of an overall electronic device (e.g., a consumer electronic device) in which the speaker component 402 is positioned, the sound hole 424 may open to another cavity inside of an overall electronic device in which the speaker assembly 400 is positioned, etc.

The example speaker assembly 400 may also, for example, comprise an air sensor 430 mechanically and/or electrically coupled to the cover 422. The air sensor 430 may, for example, be positioned adjacent to the sound hole 424. For example, the air sensor 430 may be positioned at or around the perimeter of the sound hole 424 (e.g. extending from the cover 422 toward the center of the sound hole 424, on the inner side of the cover 422 adjacent to the sound hole 424, on the upper side of the cover 422 adjacent to the sound hole 424, etc.). For example, the air sensor may be positioned within 1 mm of the sound hole 424 (or alternatively within 2 mm or 5 mm). Though the sensor 430 is only illustrated at one side of the sound hole 424, the sensor 430 may partially and/or completely surround the sound hole 424. For example, as with other sensors discussed herein, the sensor 430 may generally comprise a circular, square, or generally polygonal shape with a center hole through which air flowing through the sound hole 424 also flows.

The air sensor 430 may, for example, be electrically coupled to the substrate 407, for example directly and/or through electrically conductive features of the cover 422. As an example, the cover 422 may comprise electrical pads to which the air sensor 430 may be coupled (e.g., directly coupled) and traces to convey electrical signals between the sensor 430 and the substrate 407.

The cover 422 and/or substrate 407 generally define a cavity 427 around the speaker component 402. In accordance with various aspects of this disclosure, the air sensor 430 may be coupled to a surface of the substrate 407 and/or cover 422 at the inside of the cavity 427.

Figure 4B:
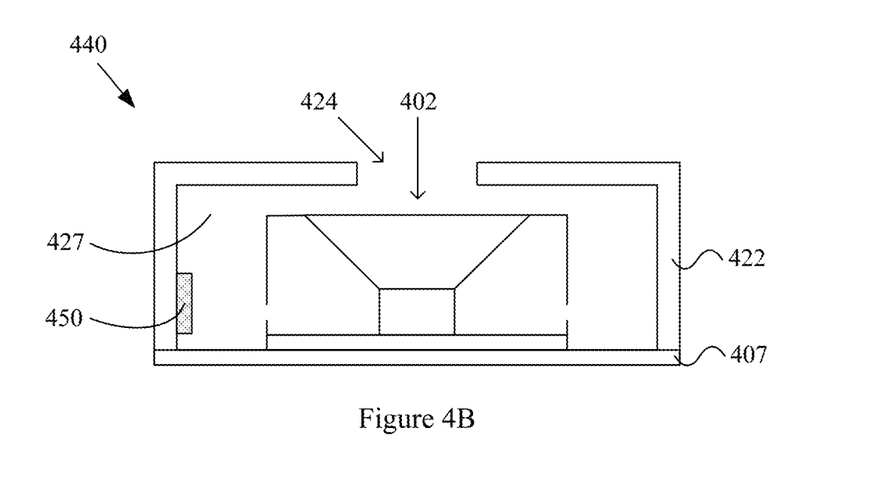

Turning next to FIG. 4B, such figure shows a block diagram (e.g., a cross-sectional view) of an example speaker assembly 440 with at least one cover-mounted air sensor, in accordance with various aspects of the present disclosure. The example speaker assembly 440 may, for example, share any or all characteristics with any other speaker assembly discussed herein (e.g., speaker assemblies 200, 240, and 280 of FIGS. 2A-2C; speaker assemblies 300 and 340 of FIGS. 3A and 3B, speaker assembly 400 of FIG. 4A, etc.).

The air sensor 430 may, for example, be mechanically and/or electrically coupled to the interior of the cover 422. Also for example, the air sensor 430 may be mechanically coupled to the interior of the cover 422 and electrically coupled to the substrate 407. The air sensor 430 may, for example, be electrically coupled to the substrate 407, for example directly and/or through electrically conductive features of the cover 422. As an example, the cover 422 may comprise electrical pads to which the air sensor 430 may be coupled (e.g., directly coupled) and traces to convey electrical signals between the sensor 430 and the substrate 407.

As illustrated, the air sensor 450 may be positioned near a port of the speaker component 402 (e.g., on a side wall of the cover 422 directly across from the port). For example, the air sensor 450 may be positioned adjacent to the port such that there are no intervening components between the air sensor 450 and the port. Additionally, for example, the air sensor 450 may be positioned within 1 mm of the port (or alternatively within 2 mm or 5 mm). For example, the air sensor 450 may be positioned adjacent to the port such that air flow through the port must generally pass over the air sensor 450.

Note that the air sensor 450 may generally be coupled to the cover 422 at any location of the cover (e.g., on an inside surface of the cover 422 or an outside surface of the cover 422). It should also be noted that, although the cover 422 of FIGS. 4A and 4B is shown as a single piece with top and side surface, such a configuration is not required. For example, the cover 422 may comprise a multi-piece structure with a single piece for the walls and a single piece for the top.

The various examples discussed to this point have generally utilized port features (e.g., between cavities, between a cavity and an external space, etc.) for air flow control. Various aspects of this disclosure also comprise the utilization of air channel features (e.g., air flow passages, tunnels, etc.). Various non-limiting examples of the utilization of air channels, for example valve-less and/or valve-controlled will now be presented.

Figure 5A:
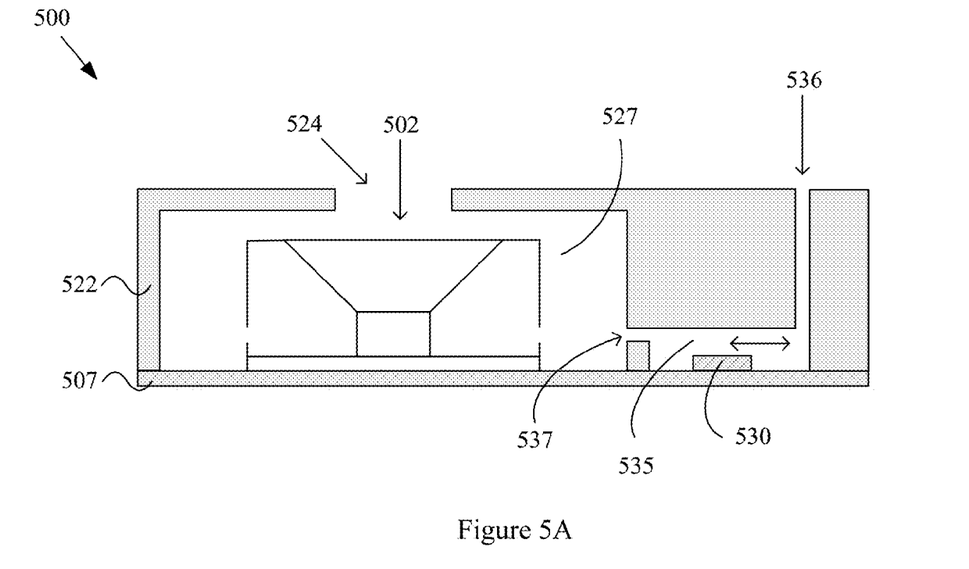
FIGS. 5A-5B show block diagrams of example electromechanical assemblies with integrated air sensors and air channels, in accordance with various aspects of the present disclosure.

Turning next to FIG. 5A, such figure shows a block diagram (e.g., a cross-sectional view) of an example electromechanical assembly 500 with at least one integrated air sensor and air channel, in accordance with various aspects of the present disclosure. The example assembly 500 may, for example, comprise a speaker assembly. The example assembly 500 may, for example, share any or all characteristics with any other speaker assembly discussed herein (e.g., speaker assemblies 200, 240, and 280 of FIGS. 2A-2C; speaker assemblies 300 and 340 of FIGS. 3A and 3B, speaker assemblies 400 and 440 of FIGS. 4A and 4B, etc.).

The example assembly 500 may, for example, comprise a substrate 507. The substrate 507 may, for example, comprise a packaging substrate, an interposer, a motherboard substrate, etc. The substrate 507 may, for example, comprise printed circuit board material, silicon, glass, metal, etc.

The example assembly 500 may also, for example, comprise a speaker component 502 that is electrically and/or mechanically coupled to the substrate 507. The speaker component 502 may, for example, share any or all characteristics with the speaker assemblies 200, 240, and 280 illustrated in FIGS. 2A-2C and discussed herein. The speaker component 502 may, for example, be coupled to the substrate 507 with or without an intervening substrate. The speaker component 502 may, for example, be coupled to the substrate 507 utilizing solder, an adhesive, etc.

The example assembly 500 may, for example, comprise a cover 522 that is coupled to the substrate 507. The cover 522 may, for example, comprise an electronic package cover, an overall cover or chassis of an electronic device in which the speaker component 502 is positioned, etc. The cover 522 may, for example, be formed of plastic, metal, silicon, MEMS material, glass, etc. The cover 522 may be coupled to the substrate 507 in any of a variety of manners. For example, the substrate 507 may be mechanically mounted in an overall device cover or chassis of which the cover 522 is at least a part, the cover 522 may be soldered or adhered to the substrate 507, etc.

The cover 522 may, for example, comprise a sound hole 524 formed therein. For example, the sound hole 524 may comprise a speaker port or sound hole in a chassis of an electronic device into which the speaker component 502 is mounted, an opening in an electronic circuit package cover of an electronic package in which the speaker component 502 is housed, etc. For example, the sound hole 524 may open to the environment outside of an overall electronic device (e.g., a consumer electronic device) in which the speaker component 502 is positioned, the sound hole 524 may open to another cavity inside of an overall electronic device in which the assembly 500 is positioned, etc. The cover 522 and/or substrate 507 generally define a cavity 527 around the speaker component 502.

The example assembly 500 may, for example, comprise an air channel 535 through which air flows between the outside of the assembly 500 and the cavity 527. Pressure differentials caused by the speaker component 502 may, for example, cause air to flow through the air channel 535. For example, in an example implementation in which the speaker component 502 pushes air out of the sound hole 524, low pressure in the cavity 527 may draw in air through the air channel 535, for example in through the exterior opening 536, through the air channel 535, and out through the interior opening 537 into the cavity 527 and/or back-cavity of the speaker unit 502. In such a configuration, the exterior opening 536 may be positioned at or near a location of an electronic device that is least likely to impart device-based heating to the air being drawn in through the exterior opening 536. In another example implementation in which the speaker component 502 draws in air through the sound hole 524, high pressure in the cavity 527 may force air out through the air channel 535, for example out of the cavity 527 through the interior opening 537 of the air channel 535, through the air channel 535, and exhausting through the exterior opening 536 of the air channel 535.

Though the air channel 535 is illustrated generally as a one-piece structure, any number of components may be assembled to form the channel 535. The example assembly 500 may also, for example, comprise an air sensor 530 positioned in the channel 535. In such an implementation, the air sensor 530 may be exposed to the air that flows through the channel 535. The air sensor 530 may, for example, be electrically and/or mechanically coupled to the substrate 507. The air sensor 530 may also, for example, be electrically and/or mechanically coupled to the cover 522 (e.g., to a portion of the cover 522 defining the air channel 535. The air sensor 530 may, for example, be implemented in a relatively flat configuration in which air generally flows over the surface of the air sensor 530. The air sensor 530 may also, for example, be implemented in a holed configuration discussed elsewhere herein, in which air passes through the center of the air sensor 530.

The air channel 535 may be formed to have various dimensions, for example depending on the pressure differentials moving air through the air channel 535, depending on desired velocity and/or volume of air through the air channel 535, etc. For example, the dimensions of the air channel 535 may be formed such that a single pulse driving the speaker component 502 will be enough to draw in air from the exterior opening 536 of the air channel 535 to the air sensor 530.

Relative to various other examples discussed herein, the example system 500 provides for minimal impact on operation of the speaker component 502. For example, the air sensor 530 generally does not interfere with air flow around the speaker component 502. Additionally, the air sensor 530 may be isolated from the effects of the speaker component 502 on the air being analyzed by the sensor 530.

Though the air sensor 530 is shown as being relatively close to (e.g., in a same package as) the air mover (e.g., the speaker component 502), the air sensor 530 may, for example, be distance from the air mover. For example, in an example phone implementation, the speaker component 502 may be generally mounted to the chassis of the phone, the air sensor 530 may be mounted to a motherboard, and an air channel may formed to provide air to the air sensor 530 on the motherboard.

The example electromechanical assembly 500 of FIG. 5A is presented utilizing a speaker component 502 as the primary mover of air to and/or from the air sensor 530. Any of a variety of other electromechanical components may also be utilized. For example, the speaker component 502 may be replaced with a vibrator, rotary fan, diaphragm-based air-mover, vibrating MEMS structure configured to move air, etc.

Figure 5B:
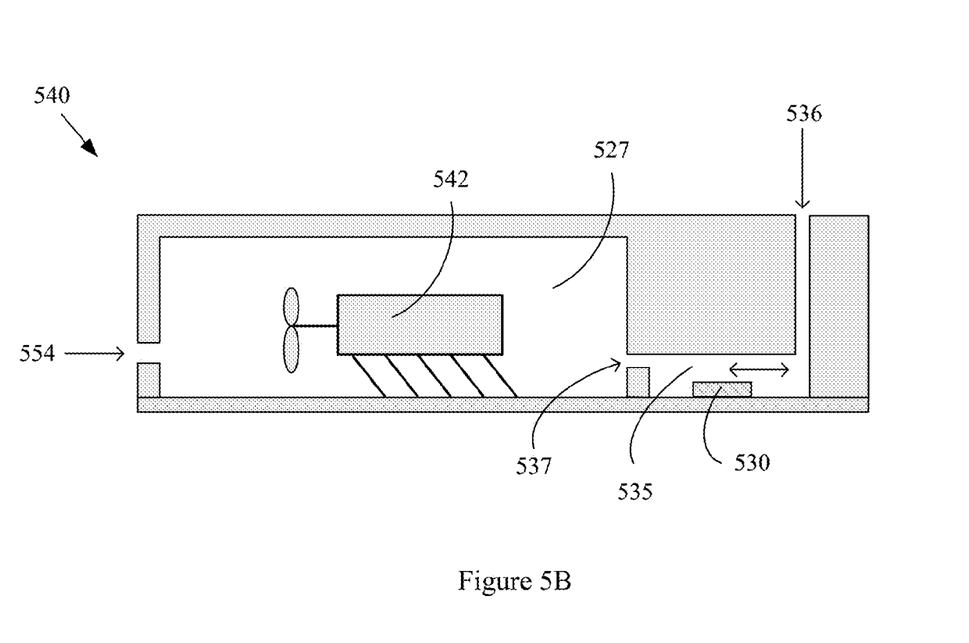

Turning next to FIG. 5B, such figure shows a block diagram (e.g., a cross-sectional view) of an example electromechanical assembly 540 with at least one integrated air sensor and air channel, in accordance with various aspects of the present disclosure. The example assembly 500 may, for example, comprise a fan assembly. The example assembly 540 may, for example, share any or all characteristics with any assembly discussed herein (e.g., speaker assemblies 200, 240, and 280 of FIGS. 2A-2C; speaker assemblies 300 and 340 of FIGS. 3A and 3B, speaker assemblies 400 and 440 of FIGS. 4A and 4B, electromechanical assembly 500 of FIG. 5A, etc.).

The example assembly 540 may, for example, comprise a fan 542. The fan 542 may, for example, comprise any or a variety of fan characteristics. For example, the fan 542 may comprise a vibrator unit (e.g., as may be utilized to vibrate a phone, watch, etc.) that comprises a rotating mass having one or more surfaces that move air. In an example implementation, the fan 542 may be run to draw in air (e.g., ambient environment air) into the exterior opening 536 of the air channel 535, through the air channel 535, through the interior opening 537 of the air channel 535, into the cavity 527 in which the fan 542 is housed, and out through the exhaust port 554. Alternatively, the fan 542 could be reversed to cause the opposite air flow.

The example assemblies 500 and 540 shown in FIGS. 5A and 5B and discussed herein utilized valve-less passive air channels, which for example allowed for multi-directional and free air flow through the air channel. Rather than valve-less passive air channels, one or more valves may be incorporated into any of the ports and/or air channels discussed herein, non-limiting examples of which will now be discussed.

Figure 6:
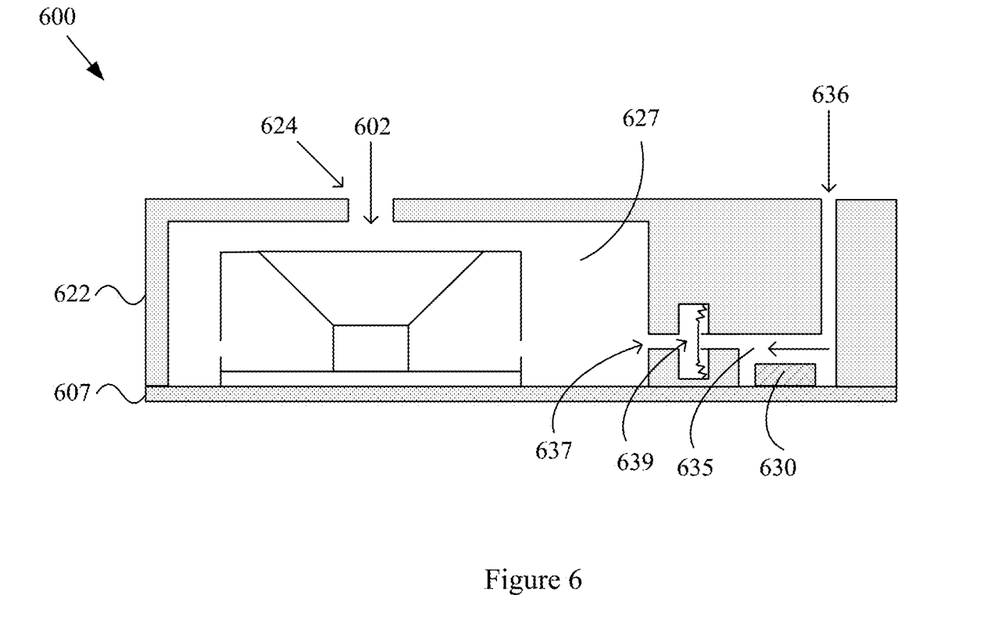
FIG. 6 shows a block diagram of an example electromechanical assembly with an integrated sensor and valve-controlled air channel, in accordance with various aspects of the present disclosure.

Turning next to FIG. 6, such figure shows a block diagram (e.g., a cross-sectional view) of an example electromechanical assembly 600 with an integrated sensor and valve-controlled air channel, in accordance with various aspects of the present disclosure. The example assembly 600 may, for example, comprise a speaker assembly. The example assembly 600 may, for example, share any or all characteristics with any other assembly discussed herein (e.g., speaker assemblies 200, 240, and 280 of FIGS. 2A-2C; speaker assemblies 300 and 340 of FIGS. 3A and 3B, speaker assemblies 400 and 440 of FIGS. 4A and 4B, electromechanical assemblies 500 and 540 of FIGS. 5A and 5B, etc.). For example, items 602, 607, 622, 624, 627, 630, 635, 636, and 637 of the example assembly 600 may share any or all characteristics with items 502, 507, 522, 524, 527, 530, 535, 536, and 537 of the example assembly 500 of FIG. 5A.

Figure 7A:
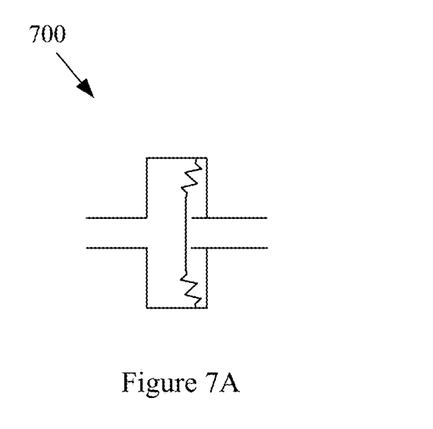
FIGS. 7A-7B show block diagrams of example passive and active valves, in accordance with various aspects of the present disclosure.

The example assembly 600 may, for example, comprise a valve 639 in the air channel 635. The valve 639 may, for example, comprise a passive valve (e.g., a valve without an actuator). An example of a normally-closed passive valve 700 is schematically illustrated at FIG. 7A. The valve 700 is held shut by spring tension and opened only when a pressure differential of the desired magnitude and direction is applied to the valve 700.

One or more passive valves 639 (and/or active valves) may, for example, be incorporated into the air channel 635 to promote the net movement of air to and across (or through) the air sensor 630. A passive valve 639 may, for example, comprise a flutter valve or any of a variety of valve configurations. A passive valve 639 controlling air flow through the air passage 635 may, for example, allow air flow in one direction to ensure that the same air is not merely being vibrated back and forth over the sensor. In other words, valve-control may cause a net air flow in a particular direction, for example drawing ambient air through the air channel 635 to the air sensor 630.

In a speaker-based implementation, a passive valve may also be tuned to activate at frequencies outside of the audio band. In such an implementation, there would be no impact on the sound system characteristics during normal use of the speaker. Then the speaker may be driven by a waveform that is designed to operate the valves, for example in an inaudible range. For example, valves may be optimized to actuate or operate in response to frequencies at 10 Hz and below, and not to operate at frequencies at 20 Hz and above. This type of implementation could be used in a channel, in a normally-sealed speaker cavity, etc. For example, the acoustic characteristics of the speaker cavity would not be altered when operating in the audio band.

Another example valve design may, for example, incorporate diaphragm technology to seal and unseal a port. For example, a diaphragm may normally rest against a port (e.g., due to native diaphragm tension, due to added springs, etc.) to seal the port unless a large enough pressure differential is experienced to move the diaphragm away from the port.

For example, in an example scenario in which the speaker component 602 pushes air out of the sound hole 624, low pressure in the cavity 627 may result in a pressure differential across the passive valve 639 that is high enough to force the valve 639 open. Air may then be drawn in through the air channel 635, for example in through the exterior opening 636, through the air channel 635, through the valve 639, and out through the interior opening 637 into the cavity 627 and/or back-cavity of the speaker unit 602. In such a scenario, ambient air (or any air to be analyzed) may thus be drawn in to the air channel 635 and to the air sensor 630.

In another example scenario in which the speaker component 602 draws in air through the sound hole 624, high pressure in the cavity 627 may hold the valve 639 closed and thus inhibit the flow of air out from the cavity 627 through the air channel 635. Note that the valve 639 may be implemented in a normally closed configuration, in which at least a minimum pressure differential threshold is necessary to open the valve 639.

Figure 7B:
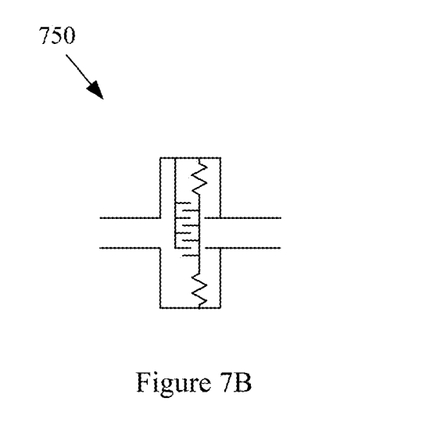

As mentioned above, the example valve 639 may comprise an active valve (e.g., a valve with an actuator). An example of an active valve 750 is provided at FIG. 7B. The example active valve 750 is electrostatically actuated (e.g., utilizing charged parallel plates) to be in an open or closed position. For example, a diaphragm may be driven against a port to seal the port, and driven away from the port to allow air to flow.

Note that the valve 639 may also operate in accordance with both active and passive principals. For example, an electrostatic actuator may operate to lock the valve in a closed state, and then operate to unlock the valve when desired to allow the valve operation to then be governed by passive forces (e.g., spring tension). Also for example, a valve may utilize heavy spring tension to remain closed (e.g., in a diaphragm or lever arm configuration) until an electrostatic force is applied to overcome the heavy spring tension at least enough to allow passive forces to effectively operate the valve. In such an implementation, energy is not consumed for the vast majority of the time during which the valve is closed.

Active valve actuation may be advantageous in any or a variety of operational scenarios. For example, when a speaker is being utilized for a telephone call or for music or another audio output purpose, the valves may be locked down to avoid undesired affects on the audio output quality. Also for example, active valve control may be utilized to control the amount of time that an air sample is available to the sensor for analysis. For example, air may be pumped into a test chamber (or channel) with the sensor, the air may then be kept in the chamber for as long as needed for an accurate measurement, and then the air may be pumped out of the chamber, for example replaced with a next sample.

Different sensors may, for example, have different respective measurement rates. In such a scenario, active valve control may be utilized to ensure that one or more sensors making the measurements are exposed to the air for a long enough amount of time. For example, a temperature sensor may take a second or perhaps a couple of seconds. In an example scenario in which a single test chamber is associated with a plurality of sensors, the amount of time that air is held in the chamber can be set to the highest respective measurement time of the sensors. Alternatively, in an example scenario in which each sensor is positioned in a respective test chamber, active valve control may be utilized to ensure that air is kept in each respective test chamber for a long enough period of time.

In an example implementation utilizing active valve actuation, valve actuation may be time-synchronized to the speaker (or other air mover) driver profile, for example rather than depending on the passive actuation discussed above. In such an example implementation, lower pressure differentials than those associated with passive valve-control may be usable, thus saving time and/or energy. Additionally, active valve actuation may be utilized to change air flow direction through a channel. For example, a valve may be actively actuated to allow air flow through a channel in a first direction during a first time period, and the valve may be actively actuated to allow air flow through the channel in a second direction opposite the first direction during a second time period. In an example implementation such operation may be utilized to expel air out of a channel to clear obstructions in the channel.

Various examples herein included the utilization of an audio speaker as an air-mover. In a speaker-based implementation, in addition to or instead of using the native activity of the speaker (e.g., to play music, for telecommunication, for alerts, etc.), one or more audio driver profiles may be utilized to drive the speaker for the purpose of moving air. The audio driver profile may be audible or inaudible, each having advantages. For example, an inaudible audio profile may be utilized to drive the speaker to move air without disturbing the user. For example, a low-frequency sine wave can be used that is below the audio range (for example below 20 Hz). Also for example, a high-frequency wave form (for example ultrasonic) may be used. Higher frequency profiles may, for example, flexibly allow asymmetrical waveforms to be used, such waveforms for example having inaudible frequency components. Inaudible waveforms may, for example, provide for the utilization of a speaker for moving air, even when the speaker is also being used for its native purpose (e.g., playing music, telecommunication, etc.), for example by superimposing audible and inaudible speaker driver signals.

Also for example, an audible audio profile may be used, for example in response to a user request for a sensor measurement. A speaker driving profile in the audible band may, for example, provide feedback to a user who requested the sensor measurement. In another example implementation, a pulse waveform (or train of pulses) may be used to advantageously generate large-amplitude pressure differentials. Such pressure differentials may then operate valves to direct air flow across the sensor. A pulse may be asymmetrical, for example generating a large pressure differential initially followed by a relatively gentle pull-back or return shape. In such a scenario, a sharp high-pressure wave may, for example, cause a pressure differential that is high enough to open a valve and draw air into a chamber (or channel).

In different operating scenarios, different driver profiles may be utilized (e.g., at different stages of the air-sensing process). For example, a relatively gentle profile (e.g., a sine wave) may be used to create a slow flow of air over the sensor. Also, for example after a measurement, a relatively violent profile (e.g., an impulse) may be used to expel particles from the test chamber.

Also as discussed herein, a vibrator may be utilized to move air for sensing. In an example implementation, the vibrator load may be configured (for example to have fan-like features) to move air when the vibrator is operated. Such a fan may, for example, comprise radial and/or axial fan features.

In a vibrator-based implementation, in addition to or instead of using the native activity of the vibrator (e.g., as a silent alert feature), one or more vibrator driver profiles may be utilized to drive the vibrator for the purpose of moving air. For example, the vibrator may be driven in a different respective manner for each of a plurality of different sensor measurement scenarios. For example, the vibrator may be driven in a steady state for a steady airflow. The vibrator may also, for example, be driven in a pulsed manner. The vibrator (or any other air mover) may, for example, be driven to create an airflow, then stopped to still the airflow, and then started again to restart the airflow.

Figure 8A:
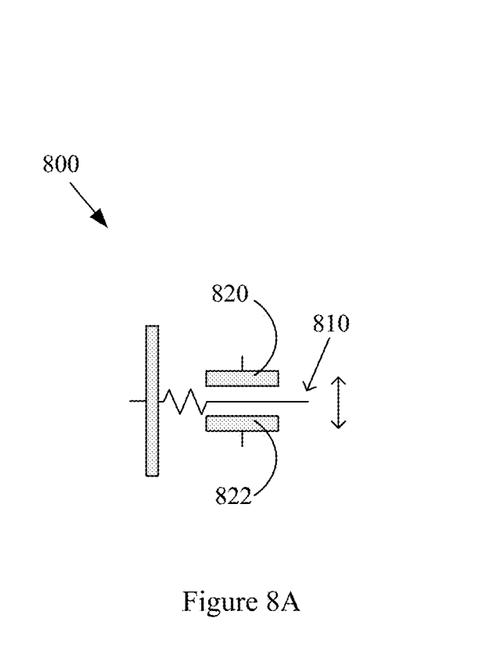
FIGS. 8A-8B show block diagrams of example electromechanical air-movers, in accordance with various aspects of the present disclosure.
Figure 8B:
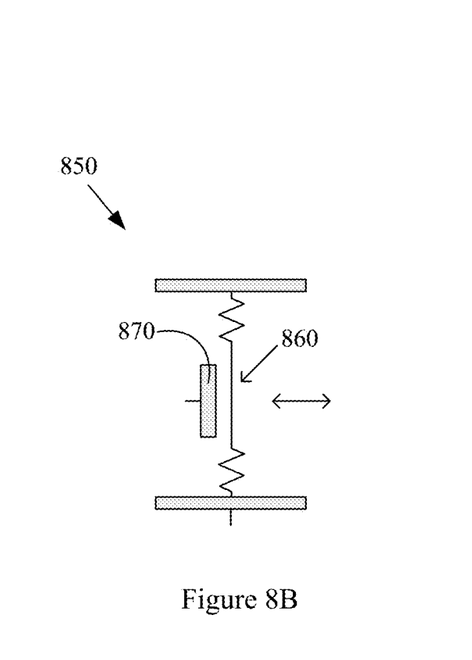

In addition to utilizing pre-existing devices (e.g., speakers, vibrators, fans, etc.) to cause air to flow over an air sensor, new air-moving actuators may be incorporated, for example for the specific purpose of moving air to be sensed. For example, ultrasonic transducers and/or MEMS transducers can be utilized. FIGS. 8A and 8B show block diagrams of example electromechanical air-movers 800 and 850, in accordance with various aspects of the present disclosure.

The example air-mover 800 of FIG. 8A, for example, comprises a mass 810 (e.g., an arm or lever) comprising spring characteristics (e.g., a return spring force as a function of beam bending). The mass 810 may, for example, be electrostatically charged. The mass 810 may then be electrostatically oscillated by one or more charged plates 820 and 822 in the direction shown by the arrows. The motion of the mass 810 may, for example, move air in the direction of the arrows and/or may also fan air in a direction orthogonal to the arrows. For example, the mass 810 may be rigid or compliant.

The example air-mover 850 of FIG. 8B, for example, comprises a mass 860 (e.g., a diaphragm) comprising spring characteristics (e.g., a return spring force as a function of displacement). The mass 860 may, for example, be electrostatically charged. The mass 860 may then be electrostatically oscillated by one or more charged plates 870 in the direction shown by the arrows. The motion of the mass 860 may, for example, move air in the direction of the arrows.

Utilization of the air flow control aspects presented herein may be performed in any of a variety of manners. For example, a device (e.g., a device 100 of FIG. 1) may comprise an air sensor module (e.g., the air sensor module 142 of FIG. 1) that operates to process data generated by the air sensor (e.g., the air sensor 157 of FIG. 1) and/or to control air flow to and/or from the sensor. For example, the air sensor module 142 may comprise instructions that, when executed by a processor (e.g., the sensor processor 130, application processor 112, etc.), control any or all of the controllable air-moving and/or airflow regulating components discussed herein (e.g., speakers, vibrators, fans, valves, etc.).

The air movement functionality, airflow control, and/or sensor analysis discussed herein may be performed in response to any of a variety of causes or conditions. For example, such functionality may be performed in response to a user command, in response to a reset or power-up condition, in response to an application request, on a regular periodic basis, on a timed schedule (periodic or aperiodic), in response to detected movement of a device, in response to a detected significant change in location, in response to a detected movement between indoor and outdoor environments, in response to a movement between a first room or building and a second room or building, etc.

The systems and methods illustrated in FIGS. 1-8, and/or presented in the discussion of such figures, were presented to illustrate various aspects of the disclosure. Any of the systems, devices, and/or assemblies presented herein may share any or all characteristics with any of the other systems, devices, and/or assemblies presented herein. Additionally, it should be understood that the various components and modules were separated out for the purpose of illustrative clarity, and that the scope of various aspects of this disclosure should not be limited by arbitrary boundaries between components or modules and/or by particular characteristics of such components or modules. For example, any one or more of the components or modules may share hardware and/or software with any one or more other components or modules.

As discussed herein, the various functional aspects discussed herein may be implemented by a pure hardware design and/or by a processor (e.g., an application or host processor, a sensor processor, etc.) executing software instructions. Similarly, other embodiments may comprise or provide a non-transitory computer readable medium and/or storage medium, and/or a non-transitory machine readable medium and/or storage medium, having stored thereon, a machine code and/or a computer program having at least one code section executable by a machine and/or a computer (or processor), thereby causing the machine and/or computer to perform the methods and/or functionality as described herein.

In summary, various aspects of this disclosure provide an air sensor with air flow control. While the foregoing has been described with reference to certain aspects and embodiments, it will be understood by those skilled in the art that various changes may be made and equivalents may be substituted without departing from the scope of the disclosure. In addition, many modifications may be made to adapt a particular situation or material to the teachings of the disclosure without departing from its scope. Therefore, it is intended that the disclosure not be limited to the particular embodiment(s) disclosed, but that the disclosure will include all embodiments falling within the scope of the appended claims.

What is claimed is:

1. An air sensor system comprising:
   a speaker cavity;
   a speaker positioned in the speaker cavity;
   an air channel through which air flows to and/or from the speaker cavity;
   a valve in the air channel; and
   an air sensor positioned in the air channel.

2. The air sensor system of claim 1, wherein the valve is an active valve.

3. The air sensor system of claim 2, wherein the valve is electrostatically actuated.

4. The air sensor system of claim 1, wherein the valve is a passive valve.

5. The air sensor system of claim 1, wherein the air channel is a one-way air channel.

6. The air sensor system of claim 5, wherein the air channel passes air to the speaker cavity, but not from the speaker cavity.

7. The air sensor system of claim 1, further comprising a sound port.

8. The air sensor system of claim 1, wherein the air sensor is one of a temperature sensor or a humidity sensor.

9. An air sensor system comprising:
   a speaker cavity;
   a speaker positioned in the speaker cavity;
   an air channel in flow communication with the speaker cavity;
   a valve in the air channel; and
   an air sensor positioned in the speaker cavity.

10. The air sensor system of claim 9, wherein:
    the speaker package comprises a port; and
    the air sensor is positioned adjacent to the port.

11. The air sensor system of claim 10, wherein the air sensor surrounds the port.

12. The air sensor system of claim 10, wherein the port is a back-cavity port.

13. The air sensor system of claim 10, wherein the port is a primary sound hole for the speaker package.

14. The air sensor system of claim 9, wherein the speaker cavity is a back cavity.

15. A personal electronic device comprising:
    an air sensor system comprising:
       an electromechanical device operable to cause an airflow;
       an air channel through which at least a portion of the airflow flows;
       a valve in the air channel; and
       an air sensor positioned in the air channel.

16. The personal electronic device of claim 15, wherein the personal electronic device comprises a handheld and/or wearable electronic device.

17. The personal electronic device of claim 15, wherein the valve is electrostatically actuated.

18. The personal electronic device of claim 15, wherein the air channel is a one-way air channel.

19. The personal electronic device of claim 15, wherein the electromechanical device comprises a speaker.

* * * * *